(12) United States Patent
Jeong et al.

(10) Patent No.: US 12,718,358 B2
(45) Date of Patent: Aug. 25, 2026

(54) SLEEP APNEA DIAGNOSTIC AUXILIARY SYSTEM USING SIMPLE SKULL X-RAY IMAGE AND METHOD FOR PROVIDING DIAGNOSTIC AUXILIARY INFORMATION USING SAME

(71) Applicant: Seoul National University Hospital, Seoul (KR)

(72) Inventors: Han-Gil Jeong, Seoul (KR); Tackeun Kim, Seongnam-Si (KR); Chang-Ho Yun, Seongnam-Si (KR)

(73) Assignee: Seoul National University Hospital, Seoul (KR)

( * ) Notice: Subject to any disclaimer, the term of this patent is extended or adjusted under 35 U.S.C. 154(b) by 275 days.

(21) Appl. No.: 18/039,646

(22) PCT Filed: Dec. 1, 2021

(86) PCT No.: PCT/KR2021/018045
§ 371 (c)(1),
(2) Date: May 31, 2023

(87) PCT Pub. No.: WO2022/119325
PCT Pub. Date: Jun. 9, 2022

(65) Prior Publication Data

US 2024/0005487 A1 Jan. 4, 2024

(30) Foreign Application Priority Data

Dec. 1, 2020 (KR) ........................ 10-2020-0166009
Oct. 29, 2021 (KR) ........................ 10-2021-0147291

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/4818* (2013.01); *G06V 10/40* (2022.01);
(Continued)

(58) Field of Classification Search
None
See application file for complete search history.

(56) References Cited

U.S. PATENT DOCUMENTS

2016/0029927 A1* 2/2016 Finkelstein .............. A61B 5/08 600/407

FOREIGN PATENT DOCUMENTS

KR 20180040287 A 4/2018
KR 20180123810 A 11/2018
KR 20190025792 A 3/2019
KR 20200063364 A 6/2020
(Continued)

OTHER PUBLICATIONS

Grad-CAM: Visual Explanations from Deep Networks via Gradient-based Localization Ramprasaath R. Selvaraju, Michael Cogswell, Abhishek Das, Ramakrishna Vedantam, Devi Parikh, Dhruv Batra (hereafter Ramp) (Year: 2016).*
(Continued)

*Primary Examiner* — Ming Shui
(74) *Attorney, Agent, or Firm* — Jackson Walker LLP

(57) ABSTRACT

The present invention relates to a sleep apnea diagnostic auxiliary system using a simple skull x-ray image, the system comprising: an input unit for receiving a simple skull x-ray image of a target patient; a prediction unit for analyzing the simple skull x-ray image to predict a possibility of the occurrence of sleep apnea of the target patient; an information providing unit for generating and providing diagnostic auxiliary information on the basis of the possibility of the occurrence of sleep apnea of the target patient; and an artificial intelligence learning model configured to train the prediction unit by using learning data including
(Continued)

simple skull x-ray images of a plurality of patients and sleep apnea diagnosis results of the patients.

11 Claims, 24 Drawing Sheets

(51) Int. Cl.

| | |
|---|---|
| ***G06V 10/40*** | (2022.01) |
| ***G16H 30/40*** | (2018.01) |
| ***G16H 50/20*** | (2018.01) |

(52) U.S. Cl.

CPC ............. *G16H 30/40* (2018.01); *G16H 50/20* (2018.01); *G06T 2207/10116* (2013.01); *G06T 2207/20081* (2013.01); *G06T 2207/20084* (2013.01); *G06T 2207/30008* (2013.01)

(56) References Cited

FOREIGN PATENT DOCUMENTS

| | | | |
|---|---|---|---|
| KR | 1020200069209 | A | 6/2020 |
| KR | 102185760 | B1 | 11/2020 |

OTHER PUBLICATIONS

Lee JG, Jun S, Cho YW, Lee H, Kim GB, Seo JB, Kim N. Deep Learning in Medical Imaging: General Overview. Korean J Radiol. Jul.-Aug. 2017;18(4):570-584. https://doi.org/10.3348/kjr.2017.18.4.570 (Year: 2017).*

Seo-Young Kim et al., “A Literature Survey of Machine Learning Based Obstructive Sleep Apnea Diagnosis Research,” Journal of The Korea Society of Computer and Information, 2020, vol. 25, No. 7, pp. 113-123.

* cited by examiner

FIG 6A

| Variable | OSA (N=2556) | No OSA (N=3035) | P-value |
|---|---|---|---|
| Age | 50.9 ± 13.8 | 47.4 ± 17.1 | <0.01 |
| Sex, male | 2000 (78.2%) | 1481 (48.8%) | <0.01 |
| Vascular risk factors | | | |
| Hypertension | 588 (23.0%) | 283 (9.3%) | <0.01 |
| Diabetes mellitus | 322 (12.6%) | 176 (5.8%) | <0.01 |
| Dyslipidemia | 545 (21.3%) | 271 (8.9%) | <0.01 |
| Other diagnosis | | | |
| Insomnia | 271 (10.6%) | 108 (3.6%) | <0.01 |
| Other sleep disorders | 214 (8.4%) | 53 (1.7%) | <0.01 |

FIG 6B

| Variable | OSA (N=2556) | No OSA (N=3035) | P-value |
|---|---|---|---|
| Other diagnosis | | | |
| Allergic rhinitis | 301 (11.8%) | 1130 (37.2%) | <0.01 |
| Chronic rhinitis | 218 (8.5%) | 554 (18.3%) | <0.01 |
| Chronic sinusitis | 193 (7.6%) | 602 (19.8%) | <0.01 |
| Deviated nasal septum | 423 (16.5%) | 666 (21.9%) | <0.01 |
| Other specified disorders of nose and nasal sinuses | 117 (4.6%) | 412 (13.6%) | <0.01 |
| Other diseases of larynx | 65 (2.5%) | 836 (27.5%) | <0.01 |
| GERD | 240 (9.4%) | 356 (11.7%) | <0.01 |
| PSG results | 2006 (78.5%) | 229 (7.5%) | <0.01 |

FIG 7

CHARACTERISTICS OF PATIENTS WITH POLYSOMNOGRAPHY RESULT

| Variable | Total (N=2235) |
| --- | --- |
| Age | 51.1 ± 13.4 |
| Sex, male | 1714 (76.7%) |
| BMI | 26.8 ± 4.6 |
| Neck circumference | 38.0 ± 4.0 |
| Waist-hip ratio | 0.9 ± 0.1 |
| Hypertension | 520 (23.3%) |
| Diabetes mellitus | 281 (12.6%) |
| Dyslipidemia | 478 (21.4%) |
| Epworth Sleepiness Scale | 9.7 ± 5.0 |
| Pittsburgh Sleep Quality Index | 7.4 ± 3.7 |
| Type of PSG: split test (vs. full) | 1120 (50.1%) |
| Time in bed, min | 369.7 ± 168.1 |
| Sleep period time, min | 347.5 ± 166.6 |
| Total sleep time, min | 290.2 ± 149.1 |
| Sleep efficacy, % | 76.7 ± 16.0 |
| Sleep latency, min | 17.0 ± 24.3 |
| Apnea-Hypopnea Index (AHI) | 33.9 ± 27.3 |
| Category of AHI | |
| - AHI < 5 | 229 (10.2%) |
| - 5 <= AHI < 15 | 478 (21.4%) |
| - 15 <= AHI < 30 | 510 (22.8%) |
| - AHI >= 30 | 1018 (45.5%) |
| Oxygen desaturation index | 27.9 ± 25.8 |

FIG 8

| Labels | Type | Loss function |
| --- | --- | --- |
| Clinical diagnosis | | |
| Any OSA vs. Normal | dichotomized | binary cross entropy |
| Moderate/Severe OSA vs. Mild OSA/Normal | dichotomized | binary cross entropy |
| Polysomnography Variables | | |
| Apnea/Hypopnea index | continuous | mean squared error |
| Apnea index | continuous | mean squared error |
| Hypopnea index with desaturation | continuous | mean squared error |
| Hypopnea index without desaturation | continuous | mean squared error |
| Respiratory disturbance index (RDI) | continuous | mean squared error |
| Lowest Oxygen Saturation | continuous | mean squared error |
| Oxygen Desaturation Index | continuous | mean squared error |
| % Time of Saturation <= 88% (% TST) | dichotomized | binary cross entropy |

FIG 12

| Predicted / Actual | No OSA | OSA |
|---|---|---|
| No OSA | 662 | 244 |
| OSA | 181 | 594 |

FIG 16
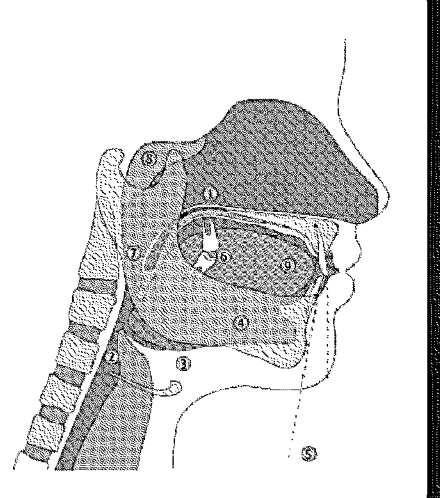
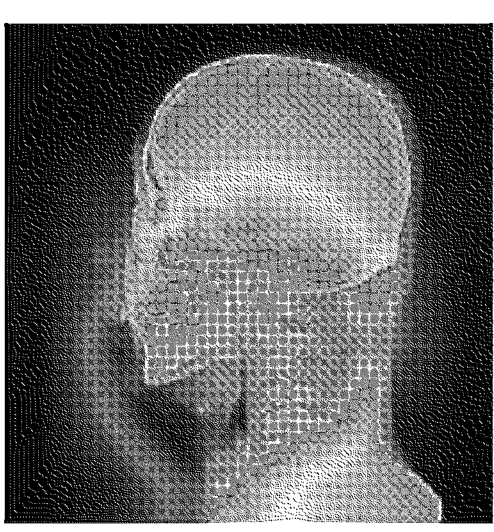

SLEEP APNEA DIAGNOSTIC AUXILIARY SYSTEM USING SIMPLE SKULL X-RAY IMAGE AND METHOD FOR PROVIDING DIAGNOSTIC AUXILIARY INFORMATION USING SAME

TECHNICAL FIELD

The present invention relates to a sleep apnea diagnostic auxiliary system using a simple skull x-ray image, and a method for providing diagnostic auxiliary information using the same.

BACKGROUND ART

Obstructive sleep apnea (OSA) is a very prevalent and pathological disease. It is important to screen patients with OSA because the patients need clear diagnostic and therapeutic measures. Polysomnography is commonly used to confirm obstructive sleep apnea, but it is time-consuming, expensive, and laborious, and is not suitable as a screening test. In addition, CT or MRI are the most accurate for evaluating anatomical abnormalities in the respiratory tract and skull and facial regions, but there are disadvantages of high radiation exposure and high cost. Therefore, there is a need for a test to screen patients with a high possibility of sleep apnea.

DISCLOSURE

Technical Problem

The present invention is directed to a diagnostic auxiliary system which is configured to predict a possibility of the occurrence of sleep apnea from a simple skull x-ray image of a patient using an artificial neural network model, and to a method for providing diagnostic auxiliary information to a clinician on the basis of the possibility of the occurrence of sleep apnea.

Technical Solution

A sleep apnea diagnostic auxiliary system using a simple skull x-ray image, the system including: a prediction unit configured to analyze the simple skull x-ray image to predict a possibility of the occurrence of sleep apnea of the target patient; an information providing unit configured to generate and provide diagnostic auxiliary information on the basis of the possibility of the occurrence of sleep apnea of the target patient; and an artificial intelligence learning model configured to train the prediction unit by using learning data including simple skull x-ray images of a plurality of patients and sleep apnea diagnosis results of respective patients.

According to an embodiment, the sleep apnea diagnosis results of the learning data may be diagnosis results based on polysomnography.

According to an embodiment, the artificial intelligence learning model may be an artificial neural network model.

According to an embodiment, the artificial neural network model may include a plurality of layers, each layer configured to extract features from the simple skull x-ray image and correlate the features with the sleep apnea diagnosis results.

According to an embodiment, the learning data further may include clinical information on the plurality of patients, and the prediction unit may be capable of predicting the possibility of the occurrence of sleep apnea in consideration of the clinical information on the target patient.

According to an embodiment, the clinical information may include at least one of an age, a gender, a genetic disease, and the presence or absence of other diseases associated with sleep apnea.

According to an embodiment, the diagnostic auxiliary information may include interpretation information indicating features of the simple skull x-ray image that are considered by the prediction unit in predicting the possibility of the occurrence of sleep apnea.

According to an embodiment, the features may be focused around the upper respiratory tract, including the tongue and pharynx, in response to anatomical abnormalities in patients with sleep apnea.

According to an embodiment, the system may further include a display unit configured to visualize, by displaying, on the simple skull x-ray image of the target patient received by the input unit, areas that affect the prediction performance of the prediction unit.

According to an embodiment, the display unit may include a gradient-weighted CAM (Grad-CAM) model.

According to an embodiment, the learning data may include data in which at least one or more techniques of angulation, zooming in or out, translocation, histogram equalizer, flipping, and adding noise have been performed on the simple skull x-ray images for the plurality of patients.

According to an embodiment, the artificial neural network model may be a CNN model.

According to an embodiment, the CNN model may be DenseNet201.

A method of providing sleep apnea diagnostic auxiliary information using a simple skull x-ray image according to an embodiment of the present invention, the method including: receiving a simple skull x-ray image of a target patient; predicting a possibility of the occurrence of sleep apnea of a target patient by analyzing the simple skull x-ray image through an artificial intelligence learning model; and generating and providing diagnostic auxiliary information on the basis of the possibility of the occurrence of sleep apnea of the target patient, wherein the artificial intelligence learning model is trained using learning data including the simple skull x-ray images of a plurality of patients and sleep apnea diagnosis results of respective patients.

According to an embodiment, a computer program stored on a computer-readable recording medium for executing the method of providing sleep apnea diagnostic auxiliary information using the simple skull x-ray image may be provided.

Advantageous Effects

According to a sleep apnea diagnostic auxiliary system using a simple skull x-ray image and a method for providing diagnostic auxiliary information using the same, the present invention can predict a possibility of the occurrence of sleep apnea from the simple skull x-ray image, which may be easily taken at a low cost, and provide diagnostic auxiliary information to a clinician on the basis thereof, thereby saving time and costs for diagnosing sleep apnea.

The present invention may dramatically increase diagnostic usefulness of a simple skull x-ray image by utilizing results of polysomnography, a functional test, beyond deep learning research using the existing image readings.

The effects of the present invention are not limited to the aforementioned effects, and other effects, which are not mentioned above, will be clearly understood by those skilled in the art from the claims.

DESCRIPTION OF DRAWINGS

In order to more clearly describe the technical solutions of the present invention or embodiments of the related art, the drawings required in the description of the embodiments are briefly introduced below. It should be understood that the following drawings are for the purpose of describing embodiments of the present specification and are not intended to be limiting. In addition, for clarity of descriptions, some elements may be illustrated in the drawings below with various variations, including exaggeration and omission.

FIGS. 6A and 6B are tables illustrating clinical information on patients used as learning data to train the prediction unit, according to an embodiment of the present invention.

FIG. 7 is a table illustrating clinical information on patients who have been tested with polysomnography, which is used as learning data to train the prediction unit, according to an embodiment of the present invention.

FIG. 8 is a table comparing the kinds, types, and loss functions of label data of a plurality of training samples for training the prediction unit, according to an embodiment of the present invention.

FIG. 12 is an error matrix of a performance metric of the artificial neural network model, according to an embodiment of the present invention.

FIG. 16 is a view comparing one of the visualized images in FIG. 14 using Grad-CAM with an anatomical image of a patient diagnosed with sleep apnea, according to an embodiment of the present invention.

MODE FOR DISCLOSURE

The technical terms used herein are merely for the purpose of describing a specific exemplary embodiment, and not intended to limit the present invention. Singular expressions used herein include plural expressions unless they have definitely opposite meanings. The terms "comprises" and/or "comprising" used in the specification specify particular features, regions, integers, steps, operations, items, and/or components, but do not exclude the presence or addition of other features, regions integers, steps, operations, items, and/or components.

Unless otherwise defined, all terms used herein including technical or scientific terms have the same meanings as meanings which are generally understood by those skilled in the art. It shall be additionally construed that terms, which are defined in dictionaries generally used, have meanings matching the related art document and currently disclosed contents, and the terms shall not be construed as ideal or excessively formal meanings unless clearly defined in the present application.

Hereinafter, embodiments of the present invention will be described in detail with reference to the drawings.

Figure 1:
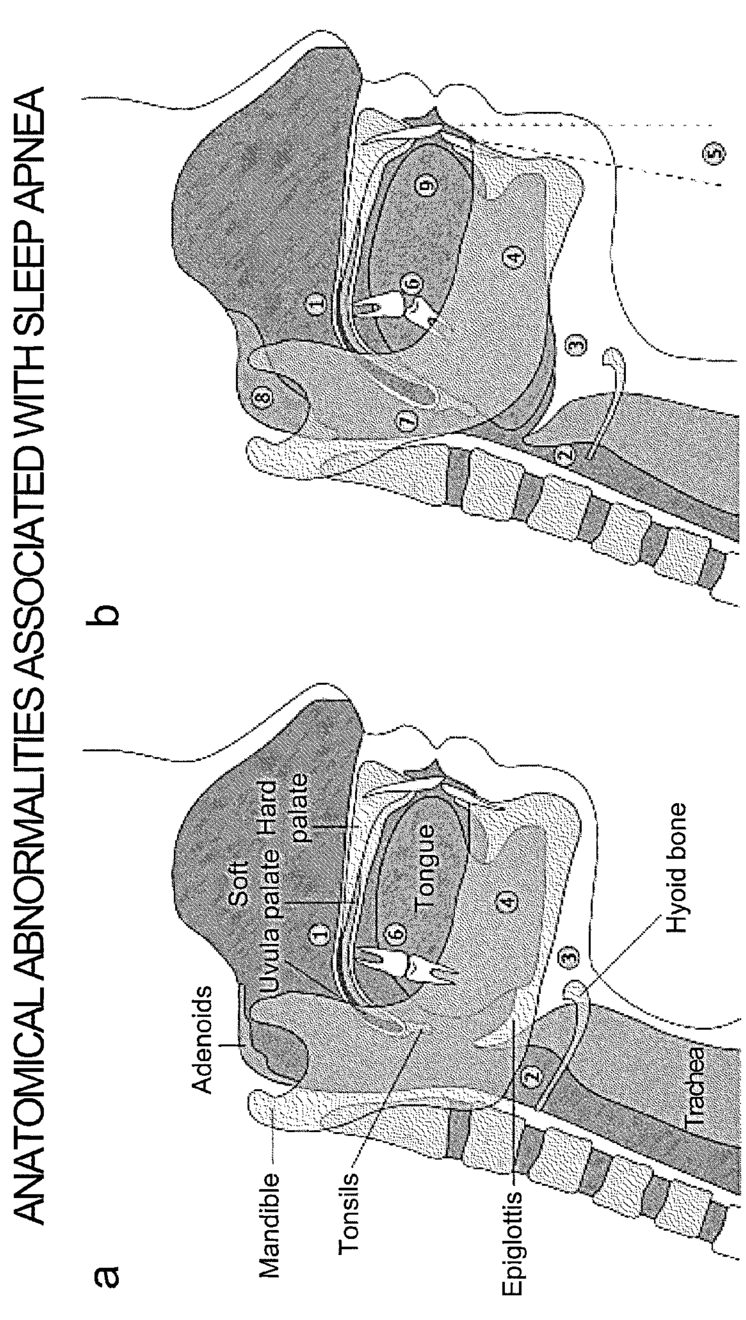
FIG. 1 is an image illustrating anatomical abnormalities related to sleep apnea.

FIG. 1 is an image illustrating anatomical abnormalities related to sleep apnea.

With reference to FIG. 1, compared to a normal person (left), a patient with sleep apnea (right) has an anatomical abnormality that results in a narrowing of the upper respiratory tract, which is a structure that begins in the nasal cavity and extends into the pharynx. Even in case that fat builds up in the neck due to obesity or tissues such as the tongue and tonsils are enlarged, a decrease in space in the throat and a narrowing of the upper respiratory tract may lead to sleep apnea. In addition, people with abnormally small jaws or short, thick necks are more prone to sleep apnea.

Figure 2:
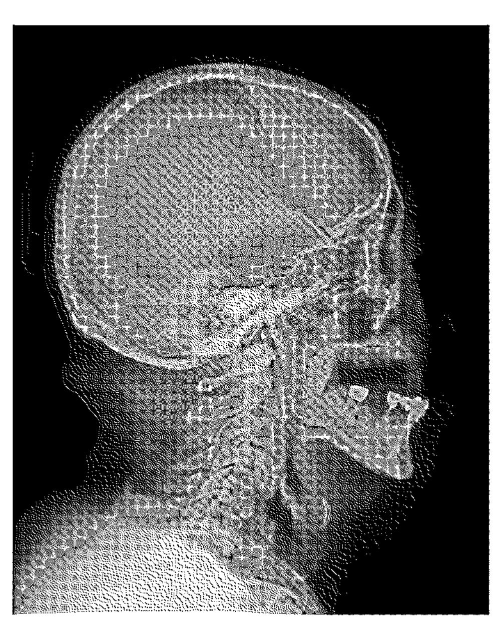
FIG. 2 is a simple skull x-ray image received by an input unit for diagnosing sleep apnea, according to an embodiment of the present invention.

FIG. 2 is a simple skull x-ray image received by an input unit for diagnosing sleep apnea, according to an embodiment of the present invention.

Obstructive sleep apnea is diagnosed by polysomnography, and there are several treatment options, including positive airway pressure therapy, lifestyle improvements, oral orthosis, and surgery. Therefore, while efforts should be made to actively identify and diagnose patients, polysomnography is not suitable as a screening test due to the time to test, cost, and effort involved.

With reference to FIG. 2, a simple skull x-ray image may be utilized as a screening test to identify patients with a high possibility of sleep apnea. The most accurate way to evaluate the anatomical abnormalities in FIG. 1 described above is to utilize CT or MRI scans, but CT or MRI scans have the disadvantage of high radiation exposure and high cost. The simple skull x-ray image is a two-dimensional x-ray image of the entire front or side of the skull of a patient obtained in a single x-ray. The simple skull x-ray has the potential to become more widely used because the simple x-ray is inexpensive and easy to take, while still providing a lot of information.

Figure 3:
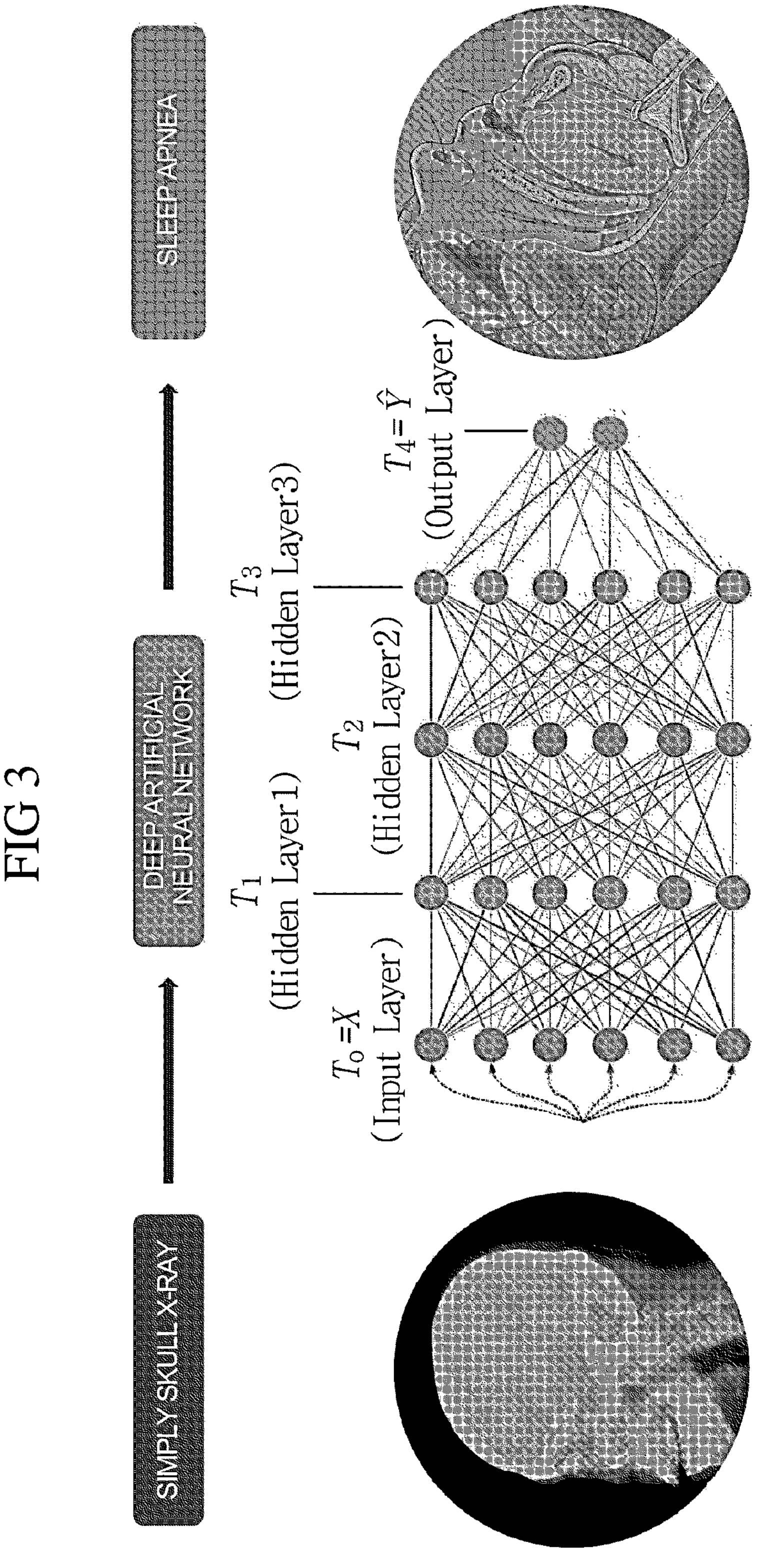
FIG. 3 is an image illustrating a process for diagnosing sleep apnea from the simple skull x-ray image in FIG. 2 using an artificial neural network model, according to an embodiment of the present invention.

FIG. 3 is an image illustrating a process for diagnosing sleep apnea from the simple skull x-ray image in FIG. 2 using an artificial neural network model, according to an embodiment of the present invention.

With reference to FIG. 3, deep learning can be utilized to diagnose sleep apnea from the simple skull x-ray image. In particular, a convolutional neural network (CNN) model may be used, which is an artificial neural network model. The CNN has the advantage of automatically extracting various hierarchical features from the image from low to high dimensions. The CNN model allows for abstraction of various features that are not quantifiable by the human eye and enables the prediction of sleep apnea from these complex relationships with high accuracy.

Figure 4:
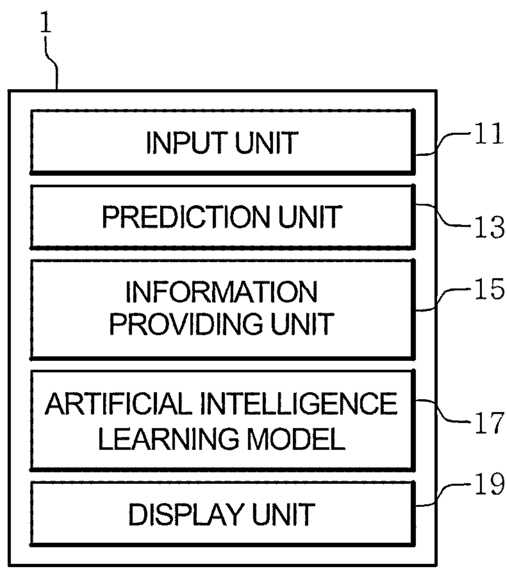
FIG. 4 is a schematic view of a sleep apnea diagnostic auxiliary system using a simple skull x-ray image, according to an embodiment of the present invention.

FIG. 4 is a schematic view of a sleep apnea diagnostic auxiliary system using a simple skull x-ray image, according to an embodiment of the present invention.

With reference to FIG. 4, a sleep apnea diagnostic auxiliary system (hereinafter referred to as a "sleep apnea diagnostic system") 1 utilizing a simple skull x-ray image may include an input unit 11, a prediction unit 13, an information providing unit 15, an artificial intelligence learning model 17, and a display unit 19.

The input unit 11 may receive an input of a simple skull x-ray image of a target patient. In an embodiment, the simple skull x-ray image may be a lateral simple skull x-ray image. The component that receives an input of a simple skull x-ray image of a target patient may be implemented with various imaging devices that may be used in the field of technology related to the present invention. In an embodiment, the input unit 11 may receive a simple skull x-ray image from a medical imaging system that takes medical images of the human skull and stores the taken images.

The prediction unit 13 may analyze the simple skull x-ray image to predict a possibility of the occurrence of sleep apnea of the target patient. The prediction unit 13 predicts whether the target patient has the possibility of the occurrence of sleep apnea with the simple skull x-ray image input from the input unit 11.

The information providing unit 15 may generate and provide diagnostic auxiliary information on the basis of the possibility of sleep apnea occurring in the target patient. The diagnostic auxiliary information may include interpretation information indicating features of the simple skull x-ray image that are considered by the prediction unit 13 in predicting the possibility of the occurrence of sleep apnea. In an embodiment, the features may be focused around the upper respiratory tract, including the tongue and pharynx, in response to anatomical abnormalities in patients with sleep apnea.

The artificial intelligence learning model 17 is configured to train the prediction unit using learning data including simple skull x-ray images of a plurality of patients and sleep apnea diagnosis results of respective patients. The sleep apnea diagnosis results of the learning data may be diagnosis results based on polysomnography. The artificial intelligence learning model may be an artificial neural network model. The artificial neural network model may include a plurality of layers, each layer configured to extract features from the simple skull x-ray image and correlate the features with the sleep apnea diagnosis results. The learning data further includes clinical information on the plurality of patients, and the prediction unit is capable of predicting the possibility of the occurrence of sleep apnea in consideration of the clinical information on the target patient. The clinical information may include at least one of an age, a gender, a genetic disease, and the presence or absence of other diseases associated with sleep apnea. The other diseases may include hypertension, diabetes mellitus, dysli-pidemia, etc. Additionally, other associated variables may include insomnia or other sleep disorders.

The display unit 19 may visualize an area that affects prediction performance of the prediction unit 13 by displaying the area in the simple skull x-ray image of the target patient input by the input unit 11. The display unit 19 may include a gradient-weighted CAM (Grad-CAM) model.

Figure 5:
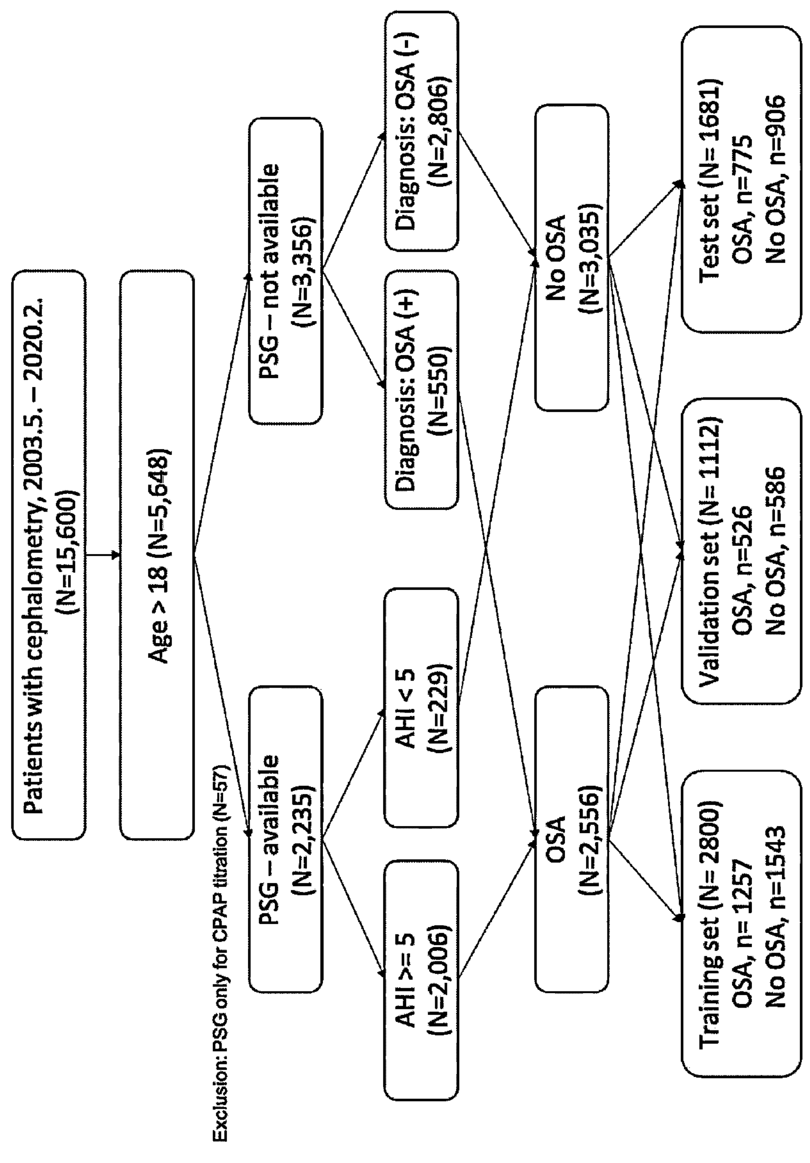
FIG. 5 is a flowchart illustrating a process of preparing and partitioning a learning dataset for training a prediction unit, according to an embodiment of the present invention.

FIG. 5 is a flowchart illustrating a process of preparing and partitioning a learning dataset for training a prediction unit, according to an embodiment of the present invention.

With reference to FIG. 5, 15,600 lateral simple skull x-ray images of patients with or without sleep apnea were collected. Then, patients were restricted to those over the age of 18 (5,648) and images from the patients were divided into those with polysomnography (2,235) and those without polysomnography (3,356). The simple skull x-ray images of patients who have been tested with polysomnography were labeled as having sleep apnea in case that the apnea-hypopnea index (AHI)>=5 (2,006), and as not having sleep apnea in case that the AHI<5 (229). The simple skull x-ray images of patients who were not tested with polysomnography were labeled as having sleep apnea in case of patients diagnosed with sleep apnea (550) and as not having sleep apnea in case of patients diagnosed without sleep apnea (2,806). Finally, the simple skull x-ray images labeled as having sleep apnea (2,556) and the simple skull x-ray images labeled as not having sleep apnea (3,035) were randomly divided into training, validation, and test datasets in a 5:2:3 ratio.

FIGS. 6A and 6B are tables illustrating clinical information on patients used as learning data to train the prediction unit, according to an embodiment of the present invention.

With reference to FIG. 6A, the group of patients diagnosed with sleep apnea was approximately 3 years older, on average, compared to the group of patients diagnosed without sleep apnea, more likely to be male, and more than twice as likely to have the vascular disease risk factors of hypertension, diabetes mellitus, and dyslipidemia. As for other associated variables, insomnia and other sleep disorders were also found to be higher.

Referring to FIG. 6*b*, patients without a diagnosis of sleep apnea were 2-3 times more likely to have rhinitis, sinusitis, and larynx disease (allergic rhinitis, chronic rhinitis, chronic sinusitis, disorders of nose and nasal sinuses and diseases of larynx) compared to patients diagnosed with sleep apnea.

FIG. 7 is a table illustrating clinical information on patients who have been tested with polysomnography, which is used as learning data to train the prediction unit, according to an embodiment of the present invention.

With reference to FIG. 7, the patients who were tested with polysomnography had a somewhat higher BMI since patients with suspected sleep apnea were primarily tested. The apnea-hypopnea index (AHI) was used to categorize the severity of sleep apnea, with normal being approximately 10% with AHI<5, mild being approximately 20% with 5<=AHI<15, and severe being approximately 20% with 15<=AHI<30. Severe cases are those with AHI>=30, which are the most common at approximately 46%.

FIG. 8 is a table comparing the kinds, types, and loss functions of label data of a plurality of training samples for training the prediction unit, according to an embodiment of the present invention.

With reference to FIG. 8, a plurality of training samples to train the prediction unit may be utilized, and each of the plurality of training samples may include a simple skull x-ray image and label data. The label data can include information for labeling the training samples by dividing patients into those diagnosed with sleep apnea and those who are healthy. In detail, depending on the severity of sleep apnea, it may be labeled as moderate/severe sleep apnea and mild sleep apnea/normal. In case that the label data includes information on whether the individual has sleep apnea or not, binary cross entropy may be used as a loss function. Additionally, in case that polysomnography information is available, the label data may include information on apnea/hypopnea index (AHI), apnea index (AI), hypopnea index with desaturation, hypopnea index without desaturation, etc. In case that the label data includes polysomnography information, mean squared error may be used as a loss function. Meanwhile, in a non-limiting example, the present invention may provide a sleep apnea prediction index (OSA-probability index) on the basis of a prediction value of the prediction unit. In a non-limiting example, a calibration or post-processing calibration may be performed to provide the prediction index as above. The calibration is to make the prediction value of the prediction unit reflect the actual probability. The post-processing calibration is to obtain a calibrated probability from the prediction probability of the model.

Figure 9:
FIG. 9 is an image of learning data augmented by various methods to train the prediction unit, according to an embodiment of the present invention.

FIG. 9 is an image of learning data augmented by various methods to train the prediction unit, according to an embodiment of the present invention.

With reference to FIG. 9, the learning data may include data in which at least one or more techniques of angulation, zooming in or out, translocation, histogram equalizer, flipping, and adding noise have been performed on simple skull x-ray images for a plurality of patients.

Figure 10:
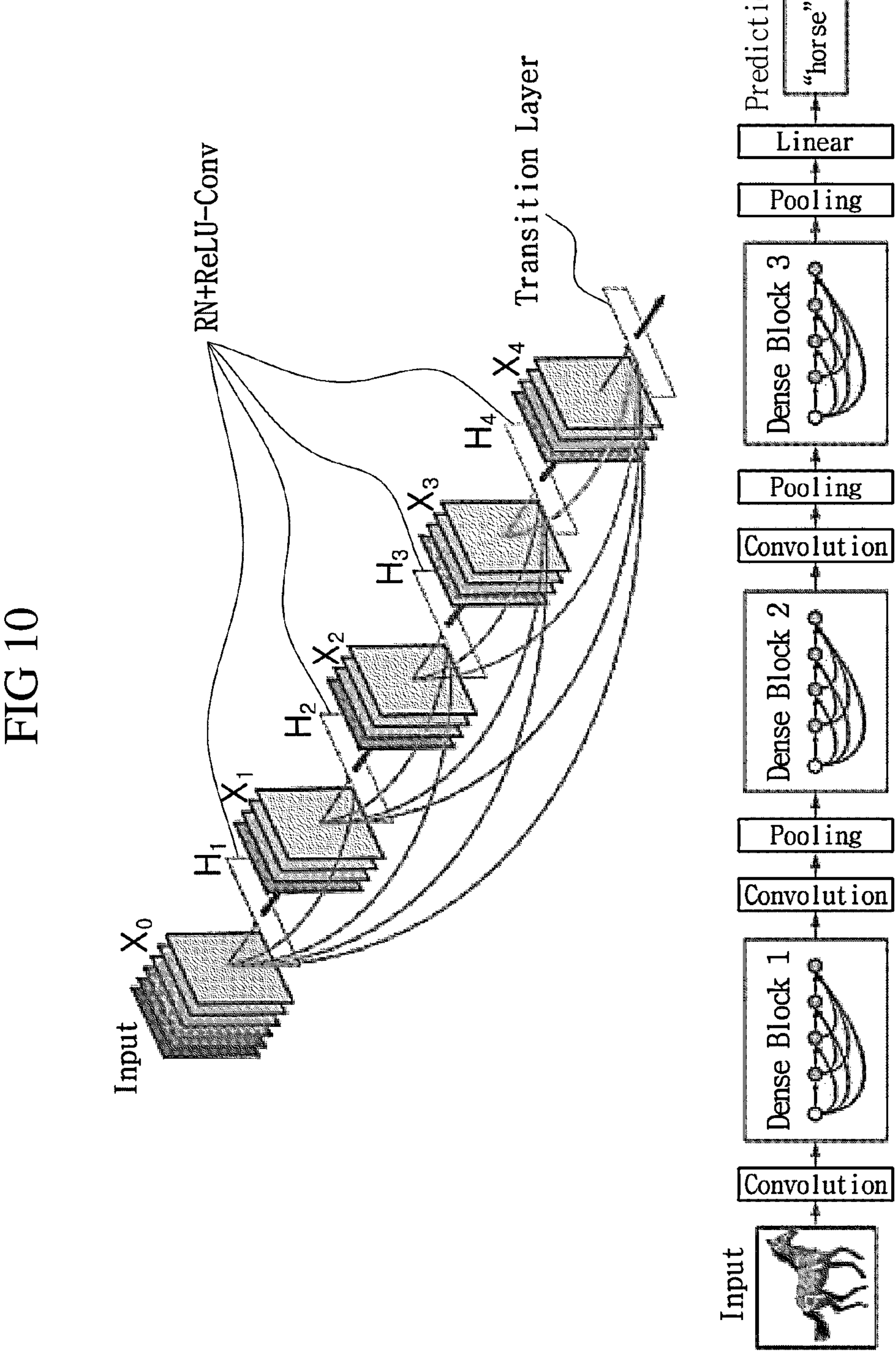
FIG. 10 is an image illustrating an architecture of DenseNet201, one of the CNN models that is capable of being used as the artificial neural network model, according to an embodiment of the present invention.

FIG. 10 is an image illustrating an architecture of DenseNet201, one of the CNN models that is capable of being used as the artificial neural network model, according to an embodiment of the present invention.

With reference to FIG. 10, an artificial neural network model in the present specification may include a deep learning model, which may be in the form of a multi-layered stack of artificial neural network. The deep learning model is configured to have the form of training a large amount of data in a deep neural network, which includes multiple layers of networks, to automatically learn the features of each image, and then train the network in a manner that minimizes errors in the objective function, i.e., the prediction accuracy.

In the present specification, the deep learning model may utilize, for example, a convolutional neural network (CNN), a deep hierarchical network (DHN), a convolutional deep belief network (CDBN), a deconvolutional deep network (DDN), and the like, but a variety of current or future deep learning models may be utilized. While the present specification exemplarily describes the use of a CNN-based artificial neural network model, the present invention is not limited thereto and may utilize a variety of current or future deep learning models. The neural network model 17 may be configured as a DenseNet structure, but is not limited thereto. The existing DenseNet is a structure that classifies 1000 labels, and is trained to classify images into sleep apnea 1 and non-sleep apnea 0 by being replaced with a single output sigmoid layer. In addition, various other neural network structures may be utilized, and in any case, the neural network may be defined to receive a particular simple skull x-ray image as input and output feature values corresponding to the probability of the occurrence of sleep apnea. A fully connected layer of the artificial neural network model has various parameters that need to be determined through learning, and converges to a single node of a target parameter to predict whether sleep apnea is present or not.

Figure 11A:
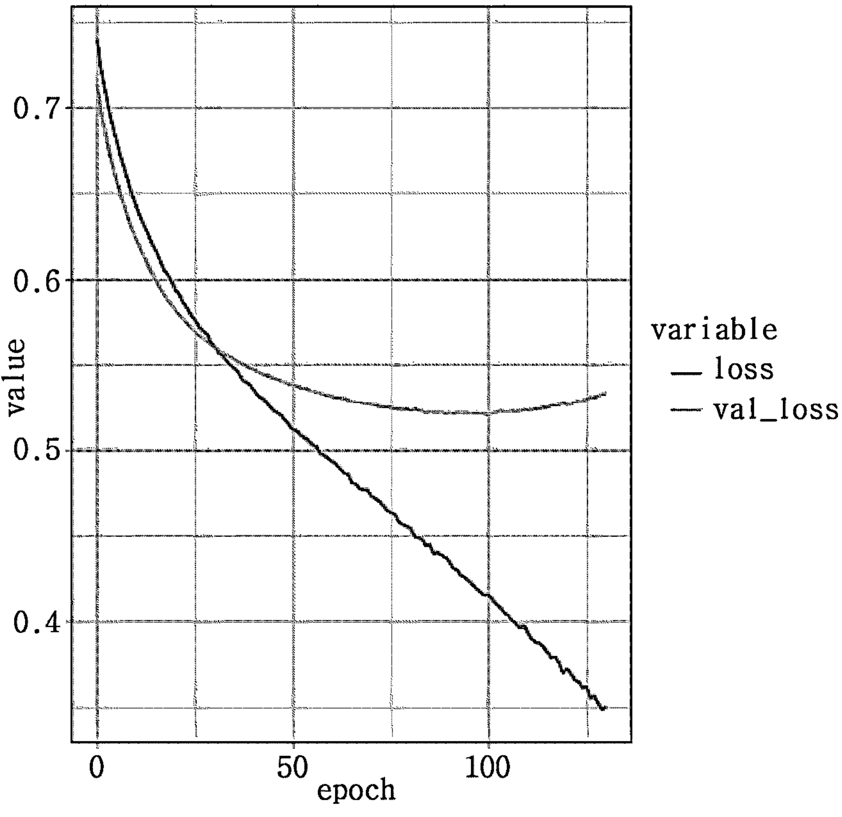
FIGS. 11A and 11B are graphs illustrating a change in each metric during a training process and final results for a training dataset and a validation dataset, according to an embodiment of the present invention.
Figure 11B:
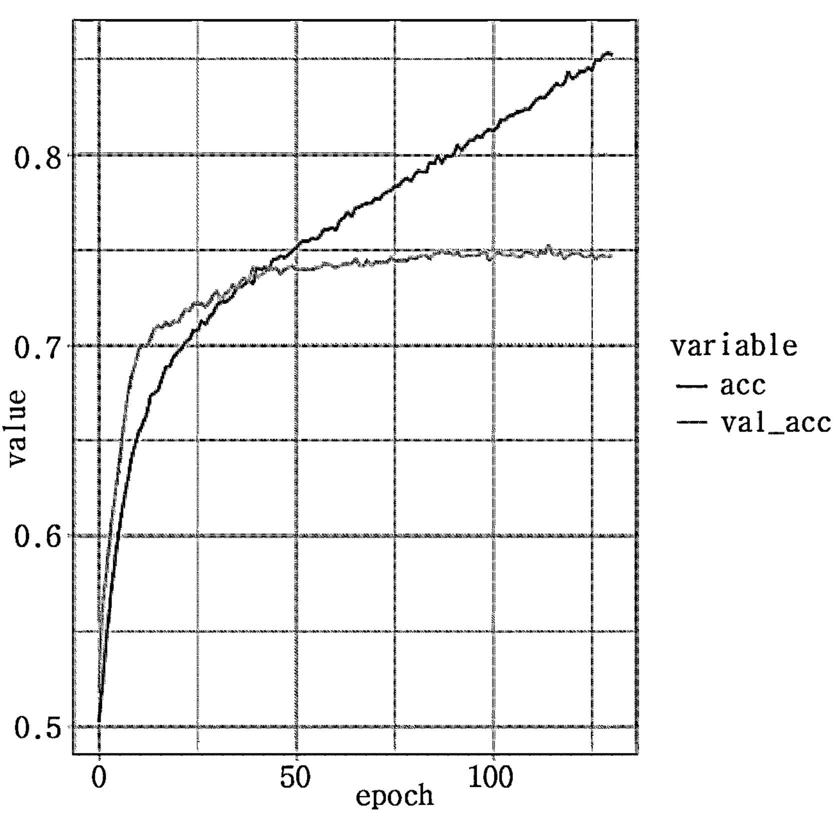

FIGS. 11A and 11B are graphs illustrating a change in each metric during a training process and final results for a training dataset and a validation dataset, according to an embodiment of the present invention.

With reference to FIGS. 11A and 11B, the red lines in the graphs represent loss and accuracy values on the training dataset, and the blue lines represent loss and accuracy values on the validation dataset. The neural network model converged to a minimum loss value for the validation dataset at 100 epochs. As the training progressed, the accuracy increased accordingly.

FIG. 12 is an error matrix of a performance metric of the artificial neural network model, according to an embodiment of the present invention.

With reference to FIG. 12, the performance of the artificial neural network model was evaluated using 30% test dataset of the learning data. 662 cases were identified as normal when actually normal, 244 cases were incorrectly identified as abnormal when actually normal, 181 cases were incorrectly identified as normal when actually sleep apnea, and 594 cases were correctly identified as sleep apnea when actually sleep apnea. Therefore, the sensitivity was 0.77, specificity was 0.73, accuracy was 0.75, and F1 score was 0.75, which was high performance when considering that only the simple skull x-ray images were used with no other information.

Figure 13A:
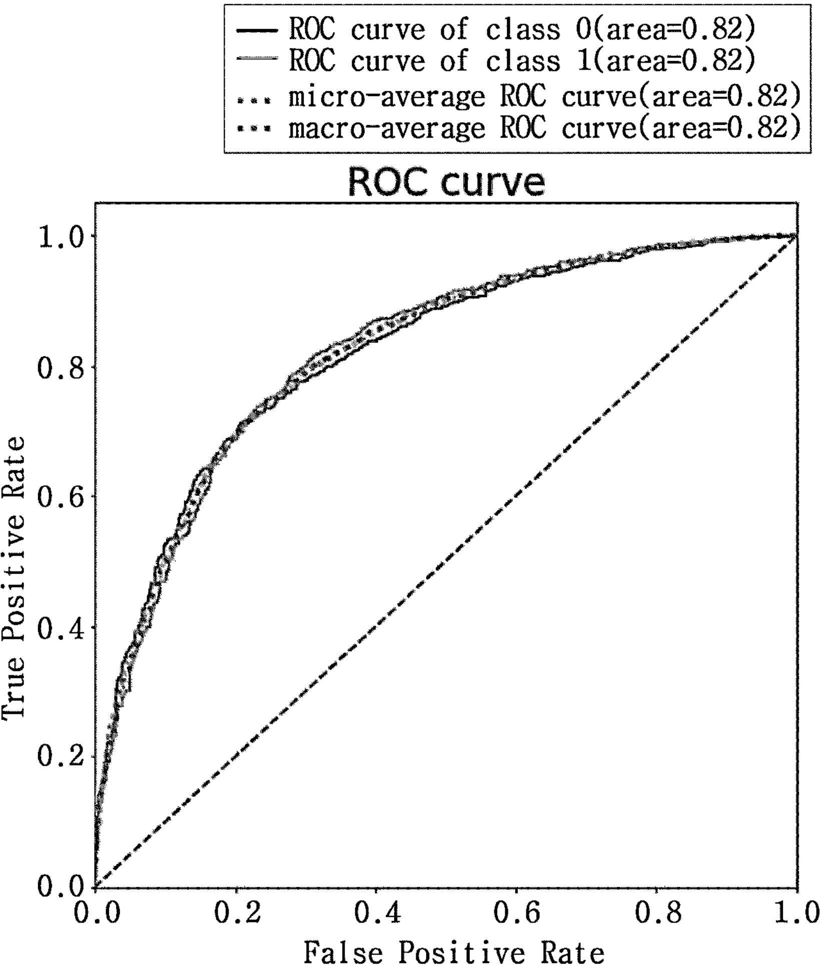
FIG. 13A is a graph illustrating ROC curves of the artificial neural network model, according to an embodiment of the present invention.

FIG. 13A is a graph illustrating ROC curves of the artificial neural network model, according to an embodiment of the present invention.

Figure 13B:
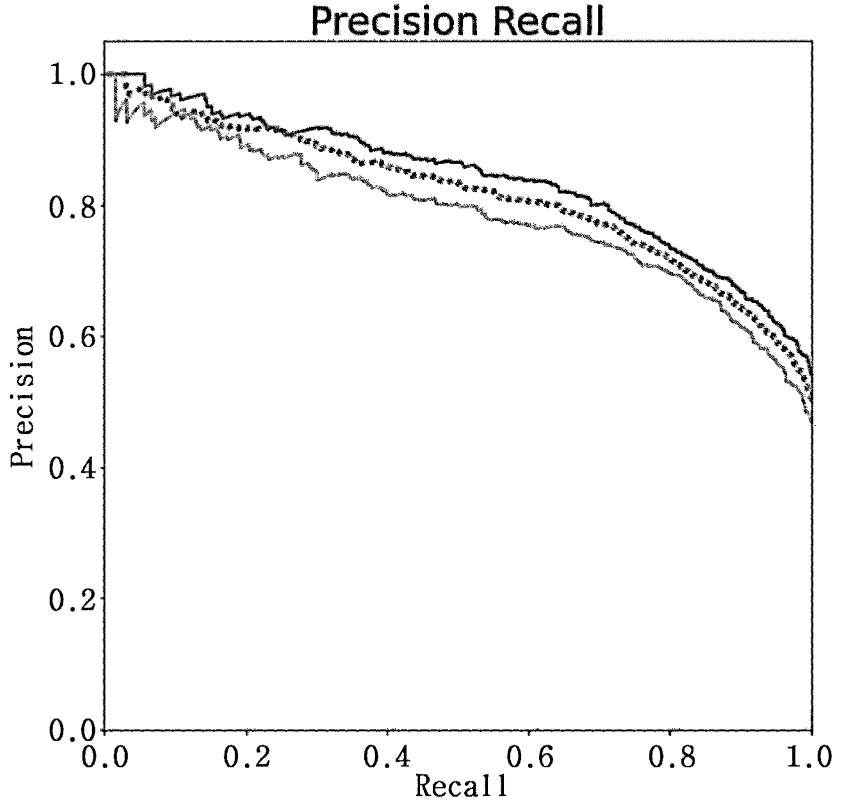
FIG. 13B is a graph illustrating precision recall curves for the artificial neural network model.

FIG. 13B is a graph illustrating precision recall curves for the artificial neural network model.

With reference to FIG. 13A and FIG. 13B, the AUC for predicting the occurrence of non-sleep apnea events and predicting the occurrence of sleep apnea events were 0.82 and 0.82, respectively, by the artificial neural network model. The class-average AUC was 0.82. The area under precision recall curves for predicting non-sleep apnea events and predicting sleep apnea events were 0.840 and 0.787, respectively. The class-average area under the precision recall curves was 0.816.

Figure 14:
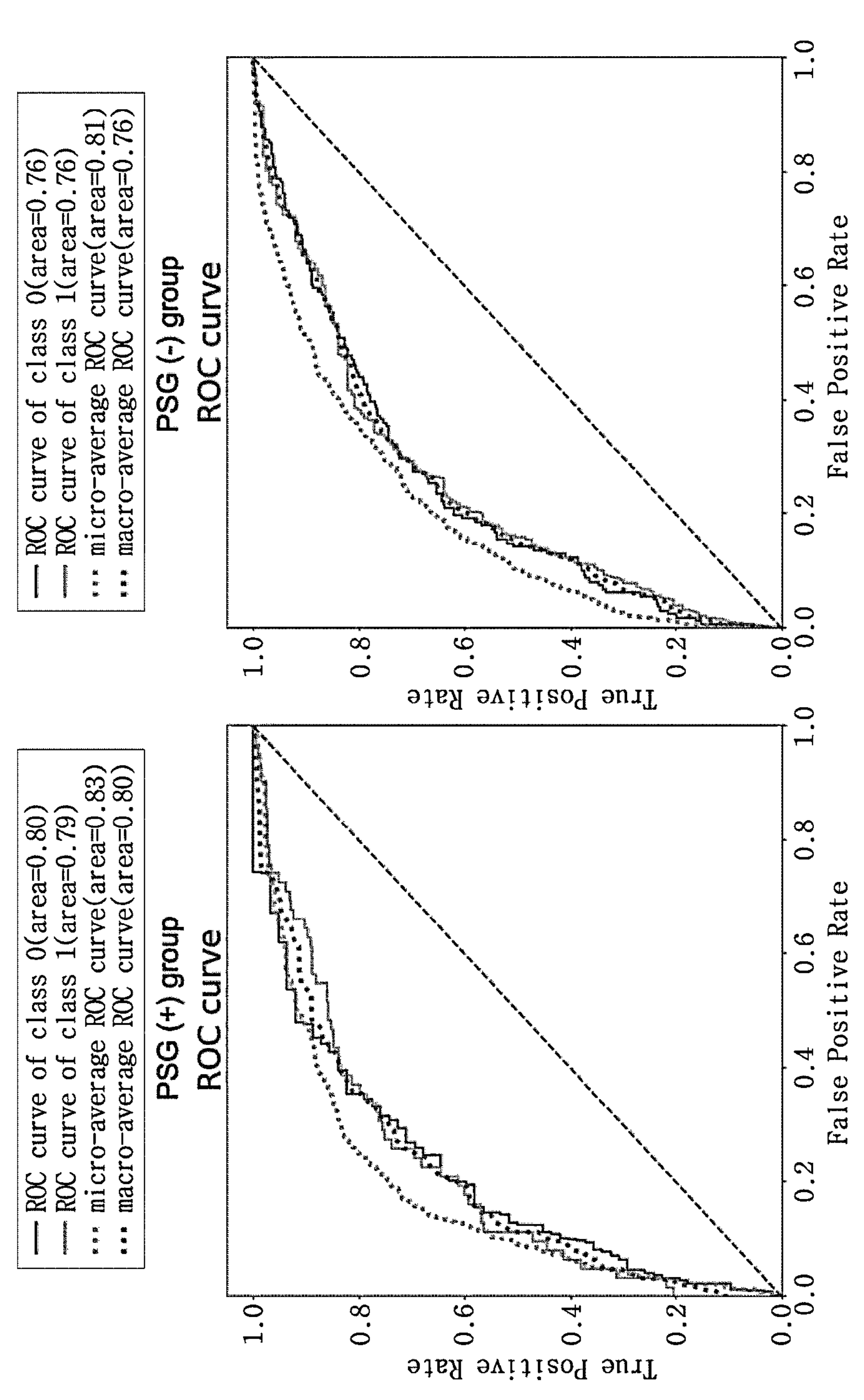
FIG. 14 is a graph comparing respective ROC curves in case that the learning data is divided into simple skull x-ray images of patients with polysomnography and simple skull x-ray images of patients without polysomnography.

FIG. 14 is a graph comparing respective ROC curves in case that the learning data in FIG. 5 is divided into simple skull x-ray images of patients with polysomnography and simple skull x-ray images of patients without polysomnography.

The AUC for predicting the occurrence of non-sleep apnea events and the occurrence of sleep apnea events in patients who was tested with polysomnography were 0.80 and respectively. The class-average AUC was 0.83 and 0.80, respectively. The AUC for predicting the occurrence of non-sleep apnea events and the occurrence of sleep apnea events in patients who was not tested with polysomnography were 0.76 and 0.76, respectively. The class-average AUC was 0.81 and 0.76, respectively, with similar performance when testing the two groups separately, so there was no significant difference.

Figure 15:
FIG. 15 is an image visualizing a portion that corresponds to a suspected area of sleep apnea to be identified, according to an embodiment of the present invention.
Figure 17A:
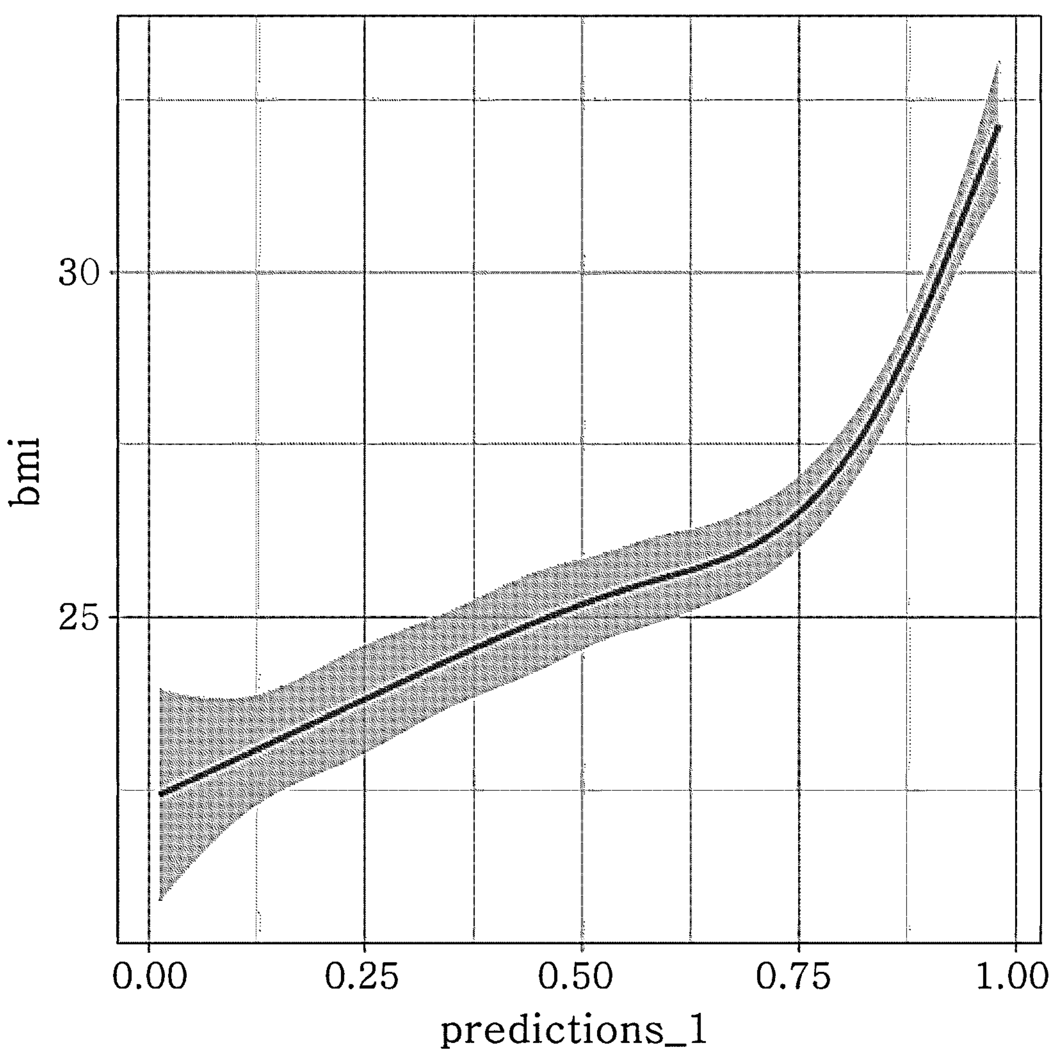
FIGS. 17A to 17D are graphs plotting correlation coefficients between predicted values of the prediction unit and body measurements traditionally associated with sleep apnea, according to an embodiment of the present invention.
Figure 17B:
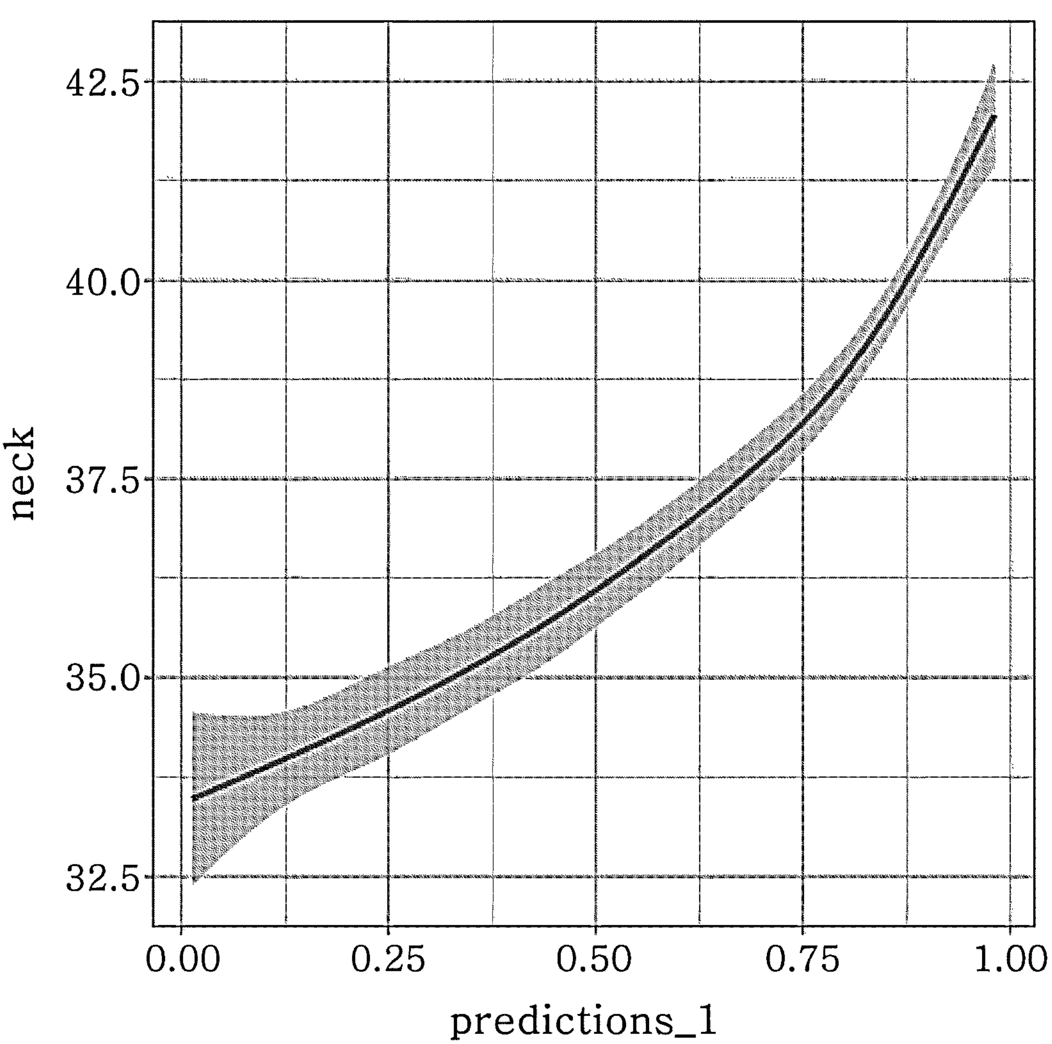
Figure 17C:
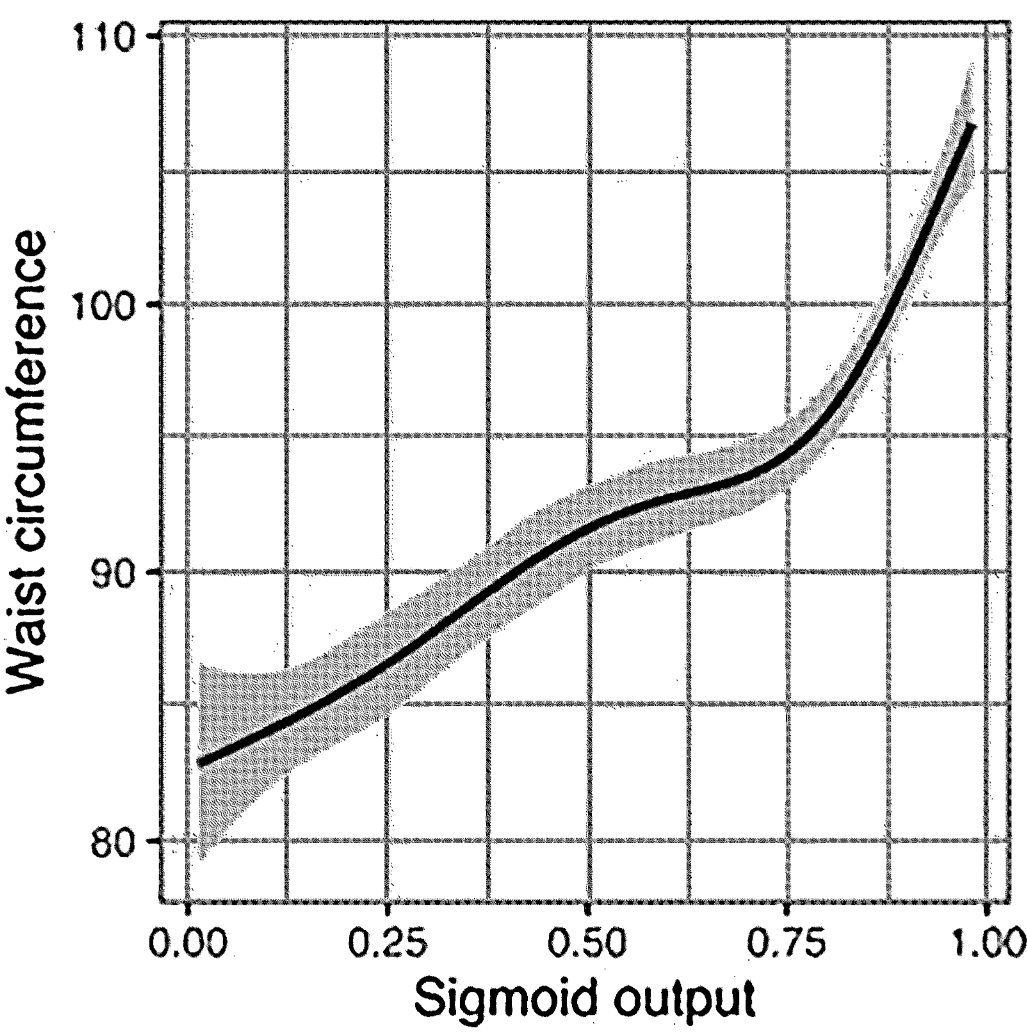
Figure 17D:
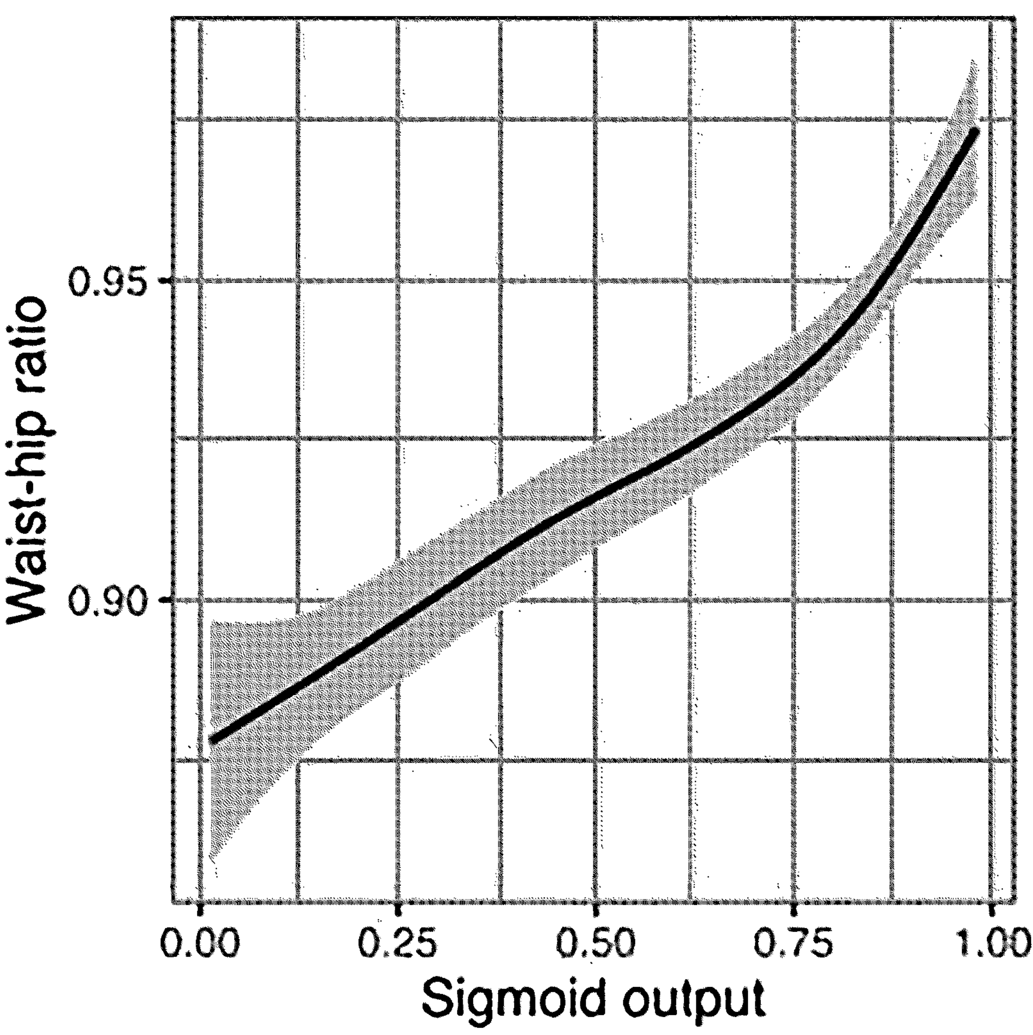

FIG. 15 is an image visualizing a portion that corresponds to a suspected area of sleep apnea to be identified, according to an embodiment of the present invention.

The sleep apnea diagnostic system 1 may further include the display unit 19, which visualizes areas affecting the prediction performance of the prediction unit 13 by displaying the areas on the simple skull x-ray image of the target patient that is input by the input unit 11. In case that the corresponding area is visualized on a display, a CAM image may be output using a gradient-weighted CAM (Grad-CAM) model.

In an embodiment of the present invention, after the prediction of the artificial neural network model is completed, the activity level for each class is displayed as an image using the internal weights and feature map, in which the feature map means the features created after performing a convolutional operation on the image. In an embodiment of the present invention, a method of obtaining the gradient-weighted CAM (Grad-CAM) is obtained by using the product of the feature map passed through the convolution and the gradient of the score (logit value) to be classified into a particular class for each grade, with the feature map passed through the convolution. In an embodiment of the present invention, the gradual-weighted CAM (Grad-CAM) may be used with almost any CNN structure, overcoming the disadvantage that the previously known structure called a graded activity map (CAM) cannot be used universally. By overlaying the gradient-weighted CAM (Grad-CAM) obtained in this manner described above at the size of the simple skull x-ray image, it may be seen which parts of the simple skull x-ray image were predicted to be a particular class.

FIG. 16 is a view comparing one of the visualized images in FIG. 16 using Grad-CAM with an anatomical image of a patient diagnosed with sleep apnea, according to an embodiment of the present invention.

With reference to FIG. 16, it may be seen that the model is heavily focused on the upper respiratory tract, particularly around the tongue and pharynx, in response to the anatomical abnormalities of the patient with sleep apnea in FIG. 1 as described above.

The prediction unit 13 extracts features from the simple skull x-ray image and predicts whether sleep apnea occurs on the basis of the extracted features, and the prediction unit 13 predicts sleep apnea when the extracted features are focused on the upper respiratory tract, particularly around the tongue and pharynx.

FIGS. 17A to 17D are graphs plotting correlation coefficients between predicted values of the prediction unit and body measurements traditionally associated with sleep apnea, according to an embodiment of the present invention.

With reference to FIGS. 17A to 17D, the correlation coefficients of the predicted values from the last node of the prediction unit with the body measurements previously associated with sleep apnea are plotted. Each of the body measurements in FIGS. 17A to 17D is a body mass index (BMI), a neck circumference, a waist circumference, and a waist-to-hip ratio. The BMI had a tendency to increase, especially above a predicted value of 0.75, while the neck circumference increased more moderately. While the prediction unit does not measure the BMI, the neck circumference, the waist circumference, and the waist-to-hip ratio by themselves, there were significant associations with the previously known associated factors.

Figure 18:
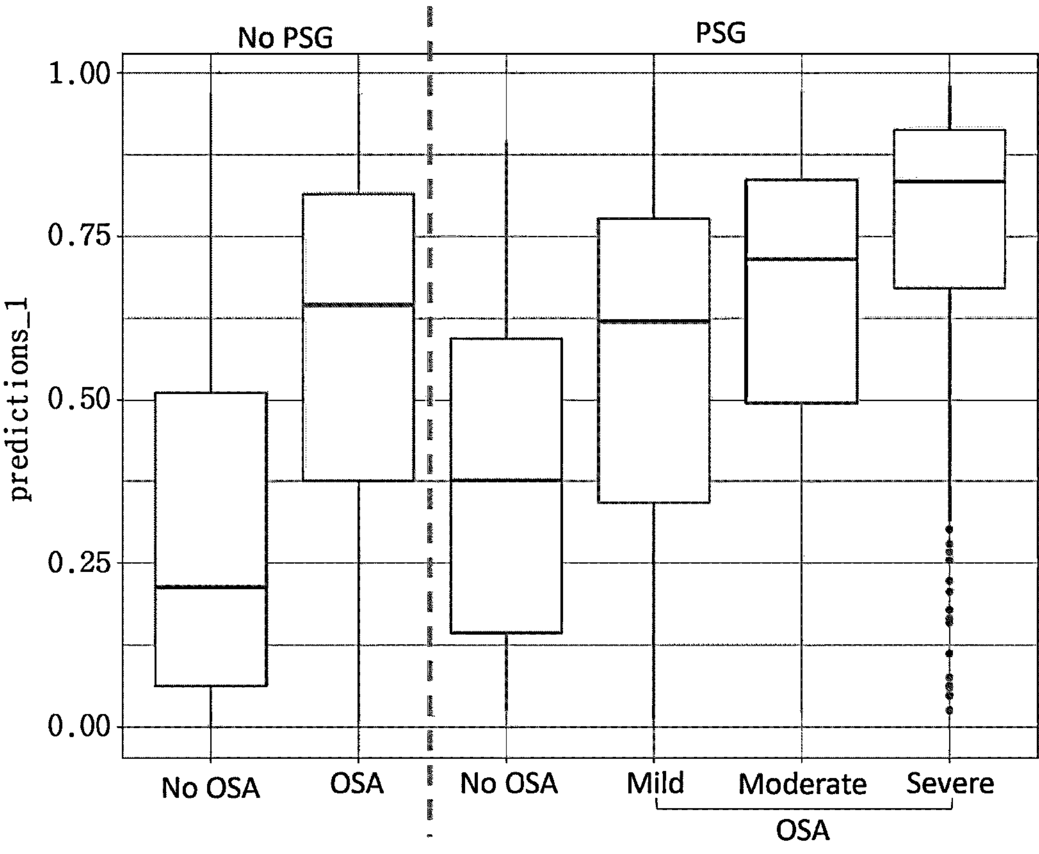
FIG. 18 is a graph illustrating a dose-response relationship, separating predicted values for patients who have been tested with polysomnography from patients who have not been tested with polysomnography, according to an embodiment of the present invention.

FIG. 18 is a graph illustrating a dose-response relationship, separating predicted values for patients who have been tested with polysomnography from patients who have not been tested with polysomnography, according to an embodiment of the present invention.

With reference to FIG. 18, the left side of the red line shows a comparison of predicted values for patients who were not tested with polysomnography, and the right side of the red line shows results for patients who were tested with polysomnography. The prediction unit was trained to predict only whether sleep apnea was present or absent without categorizing the severity, but the prediction values of the prediction unit had an increasing tendency as sleep apnea became more severe. It may be interpreted that the stronger the prediction unit predicts obstructive sleep apnea, the more likely the patient is to have severe sleep apnea.

A method of providing sleep apnea diagnostic auxiliary information using a simple skull x-ray image according to another aspect of the present invention, the method including: receiving a simple skull x-ray image of a target patient; predicting a possibility of the occurrence of sleep apnea of a target patient by analyzing the simple skull x-ray image through an artificial intelligence learning model; and generating and providing diagnostic auxiliary information on the basis of the possibility of the occurrence of sleep apnea of the target patient, in which the artificial intelligence learning model is trained using learning data including the simple skull x-ray images of a plurality of patients and sleep apnea diagnosis results of respective patients. Additionally, the method may further include a display step of visualizing, by displaying, on the simple skull x-ray image of the target patient received by the input unit, areas that affect the prediction performance of the artificial neural network model.

According to the sleep apnea diagnostic auxiliary system using a simple skull x-ray image and the method for providing diagnostic auxiliary information using the same, as described above, the present invention may predict a possibility of the occurrence of sleep apnea from the simple skull x-ray image, which may be easily taken at a low price and provide a lot of information, and provide diagnostic auxiliary information to a clinician on the basis of the prediction, thereby saving time through short inference time.

The present invention may dramatically increase diagnostic usefulness of a simple skull x-ray image by utilizing results of polysomnography, a functional test, beyond deep learning research using the existing image readings.

The operations of the method of providing sleep apnea diagnostic auxiliary information using a simple skull x-ray image according to the embodiments described above may be implemented at least in part as a computer program and recorded on a computer-readable recording medium. For example, it may be implemented with a program product configured as a computer-readable medium including program code, which may be executed by a processor to perform any or all of the steps, operations, or processes described.

The method of providing sleep apnea diagnostic auxiliary information using a simple skull x-ray image, according to another aspect of the present invention, may be performed by a computing device including a processor. The computing device may be a computing device, such as a desktop computer, a laptop computer, a notebook, a smartphone, or the like, or any device that may be integrated therewith. A computer is a device that has one or more alternative and special-purpose processors, memory, storage, and networking components (either wireless or wired). The computer may execute an operating system, such as, for example, an operating system compatible with Microsoft's Windows, Apple's OS X or iOS, a Linux distribution, or Google's Android OS.

The computer-readable recording medium includes any kind of recording identification device on which data readable by the computer is stored. Examples of computer-readable storage media include ROM, RAM, CD-ROM, magnetic tape, floppy disks, and optical data storage identification devices. In addition, the computer-readable recording medium may be distributed across a computer system that is networked, so that computer-readable code may be stored and executed in a distributed manner. Further, the functional program, code, and code segment to implement the embodiments will be readily understood by those skilled in the art to which the embodiments belong.

The present invention has been described above with reference to the embodiments illustrated in the drawings, which are just for illustration, and those skilled in the art will understand that various modifications and variations of the embodiments are possible. However, such modifications should be considered to be within the technical protection scope of the present invention. Accordingly, the true technical protection scope of the present disclosure should be determined by the technical spirit of the appended claims.

INDUSTRIAL APPLICABILITY

The sleep apnea diagnostic auxiliary system using a simple skull x-ray image of embodiments of the present invention and a method of providing diagnostic auxiliary information using the system can predict the possibility of the occurrence of sleep apnea from the simple skull x-ray image of a patient using an artificial neural network model, and provide diagnostic auxiliary information to a clinician on the basis of the prediction. Therefore, the time and costs of diagnosing sleep apnea may be reduced.

The invention claimed is:

1. A sleep apnea diagnostic auxiliary system using a simple skull x-ray image, the system comprising:

an input unit configured to receive a simple skull x-ray image of a target patient;

a prediction unit configured to analyze the simple skull x-ray image to predict a possibility of the occurrence of sleep apnea of the target patient, wherein the prediction unit predicts the possibility in response to anatomical abnormalities of a patient with sleep apnea;

an information providing unit configured to generate and provide diagnostic auxiliary information on the basis of the possibility of the occurrence of sleep apnea of the target patient; and an artificial intelligence learning model configured to train the prediction unit by using learning data including simple skull x-ray images of a plurality of patients and sleep apnea diagnosis results of respective patients, wherein the artificial intelligence learning model is a convolutional neural network model configured to automatically extract hierarchical features from low dimensions to high dimensions from the simple skull x-ray image, wherein the hierarchical features include features that are not quantifiable by a human eye, wherein the diagnostic auxiliary information comprises interpretation information indicating features of the simple skull x-ray image considered by the prediction unit in predicting the possibility of the occurrence of sleep apnea, and wherein the features of the simple skull x-ray image are focused around the upper respiratory tract, including the tongue and pharynx, in response to anatomical abnormalities of a patient with sleep apnea.

2. The sleep apnea diagnostic auxiliary system of claim 1, wherein the sleep apnea diagnostic results of the learning data is diagnostic results based on polysomnography.

3. The sleep apnea diagnostic auxiliary system of claim 1, wherein the artificial intelligence learning model is an artificial neural network model.

4. The sleep apnea diagnostic auxiliary system of claim 3, wherein the artificial neural network model comprises a plurality of layers, and wherein each layer is configured to extract features from the simple skull x-ray image and correlate the features with the sleep apnea diagnostic results.

5. The sleep apnea diagnostic auxiliary system of claim 1, wherein the learning data further comprises clinical information on the plurality of patients, and wherein the prediction unit predicts the possibility of the occurrence of sleep apnea in consideration of the clinical information of the target patient.

6. The sleep apnea diagnostic auxiliary system of claim 5, wherein the clinical information comprises at least one of a patient's age, gender, genetic disease, and the presence or absence of other diseases associated with sleep apnea.

7. The sleep apnea diagnostic auxiliary system of claim 3, further comprising a display unit configured to visualize areas affecting the prediction performance of the prediction unit by displaying the areas on the simple skull x-ray image of the target patient received by the input unit.

8. The sleep apnea diagnostic auxiliary system of claim 7, wherein the display unit comprises a gradient-weighted CAM (Grad-CAM) model.

9. The sleep apnea diagnostic auxiliary system of claim 1, wherein the learning data comprises data in which at least one or more techniques of angulation, zooming in or out, translocation, histogram equalizer, flipping, and adding noise have been performed on the simple skull x-ray images for the plurality of patients.

10. A method of providing sleep apnea diagnostic auxiliary information using a simple skull x-ray image performed by a processor, the method comprising:

receiving a simple skull x-ray image of a target patient, wherein the predicting is performed in response to anatomical abnormalities of a patient with sleep apnea;

predicting a possibility of the occurrence of sleep apnea of a target patient by analyzing the simple skull x-ray image through an artificial intelligence learning model; and generating and providing diagnostic auxiliary information on the basis of the possibility of the occurrence of sleep apnea of the target patient, wherein the artificial intelligence learning model is trained using learning data including the simple skull x-ray images of a plurality of patients and sleep apnea diagnosis results of respective patients, wherein the artificial intelligence learning model is a convolutional neural network model configured to automatically extract hierarchical features from low dimensions to high dimensions from the simple skull x-ray image, wherein the hierarchical features include features that are not quantifiable by a human eye, and wherein the diagnostic auxiliary information comprises interpretation information indicating features of the simple skull x-ray image considered by the artificial intelligence learning model in predicting the possibility of the occurrence of sleep apnea, wherein the features of the simple skull x-ray image are focused around the upper respiratory tract, including the tongue and pharynx, in response to anatomical abnormalities of a patient with sleep apnea.

11. A non-transitory computer-readable recording medium storing a computer program that, when executed by a processor, causes the processor to perform the method of providing sleep apnea diagnostic auxiliary information using the simple skull x-ray image according to claim 10.

* * * * *